(12) United States Patent
Wessendorf et al.

(10) Patent No.: US 8,285,394 B1
(45) Date of Patent: Oct. 9, 2012

(54) DEMULTIPLEXER CIRCUIT FOR NEURAL STIMULATION

(75) Inventors: Kurt O. Wessendorf, Albuquerque, NM (US); Murat Okandan, Edgewood, NM (US); Sean Pearson, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 508 days.

(21) Appl. No.: 12/502,698

(22) Filed: Jul. 14, 2009

Related U.S. Application Data (63) Continuation-in-part of application No. 11/588,905, filed on Oct. 27, 2006, now Pat. No. 8,000,804.

(51) Int. Cl.
*A61N 1/05* (2006.01)

(52) U.S. Cl. ............ 607/116; 607/53; 607/54; 607/115; 370/536

(58) Field of Classification Search .......... 370/532–546; 607/53–54, 115–116
See application file for complete search history.

(56) References Cited

U.S. PATENT DOCUMENTS

| | | | |
|---|---|---|---|
| 5,935,155 A | 8/1999 | Humayun et al. | |
| 6,658,299 B1 | 12/2003 | Dobelle | |
| 6,853,047 B1 * | 2/2005 | Comeau et al. | 257/500 |
| 7,103,416 B2 | 9/2006 | Ok et al. | |
| 7,248,928 B2 | 7/2007 | Yagi | |
| 7,263,403 B2 | 8/2007 | Greenberg et al. | |
| 7,337,008 B2 | 2/2008 | Terasawa et al. | |
| 7,499,754 B2 | 3/2009 | Greenberg et al. | |
| 2001/0053161 A1 * | 12/2001 | Tomizawa et al. | 370/538 |
| 2006/0106432 A1 * | 5/2006 | Sawan et al. | 607/54 |

OTHER PUBLICATIONS

Liu, Wentai et al., "A Neuro-Stimulus Chip with Telemetry Unit for Retinal Prosthetic Device", IEEE Journal of Solid-State Circuits, vol. 35, No. 10, Oct. 2000, pp. 1487-1497.
Weiland, James D. et al., "Visual Prosthesis", Proceedings of the IEEE, vol. 96, No. 7, Jul. 2008, pp. 1076-1084.
Weiland, James D. et al., "Systems Design of a High Resolution Retinal Prosthesis", Proceedings of the IEEE International Electron Devices Meeting, Dec. 15-17, 2008, pp. 1-4.

* cited by examiner

*Primary Examiner* — Rex R Holmes
(74) *Attorney, Agent, or Firm* — Kerry Kampschmidt (57) ABSTRACT

A demultiplexer circuit is disclosed which can be used with a conventional neural stimulator to extend the number of electrodes which can be activated. The demultiplexer circuit, which is formed on a semiconductor substrate containing a power supply that provides all the dc electrical power for operation of the circuit, includes digital latches that receive and store addressing information from the neural stimulator one bit at a time. This addressing information is used to program one or more $1:2^N$ demultiplexers in the demultiplexer circuit which then route neural stimulation signals from the neural stimulator to an electrode array which is connected to the outputs of the $1:2^N$ demultiplexer. The demultiplexer circuit allows the number of individual electrodes in the electrode array to be increased by a factor of $2^N$ with N generally being in a range of 2-4.

21 Claims, 7 Drawing Sheets

DEMULTIPLEXER CIRCUIT FOR NEURAL STIMULATION

CROSS REFERENCE TO RELATED APPLICATIONS

This is a continuation-in-part of application Ser. No. 11/588,905, filed Oct. 27, 2006 now U.S. Pat. No. 8,000,804, which is incorporated herein by reference.

GOVERNMENT RIGHTS

This invention was made with Government support under Contract No. DE-AC04-94AL85000 awarded by the U.S. Department of Energy (DOE), and under cooperative research and development agreement (CRADA) No. ORNL01-0625 with Second Sight Medical Products, Inc. The Government has certain rights in the invention.

FIELD OF THE INVENTION

The present invention relates in general to demultiplexer circuits, and in particular to a demultiplexer circuit for use with a neural stimulator such as a retinal prosthesis.

BACKGROUND OF THE INVENTION

Neural implant technology is being developed to address many types of neural illnesses including deafness, blindness, impaired motor control, etc., and can have a profound effect in increasing the abilities of persons affected by such neural illnesses. In the development of neural prostheses, there is a need to increase the number of electrodes which are used for neural stimulation beyond that which are presently available. This is especially the case for retinal prostheses (also termed visual prostheses) where simulations have indicated that up to one thousand neural stimulation electrodes will be required to provide the ability to read and to recognize faces.

The present invention addresses this need for an increased number of neural stimulation electrodes by providing a demultiplexer circuit which can be used in conjunction with a conventional neural prosthesis (also termed a neural stimulator) to increase the number of electrodes that can be actuated by a factor of $2^N$ with N being an integer which is generally in the range of 2-4. This can be used, for example, to scale up a conventional 60-electrode retinal prosthesis, which is currently being used for clinical trials, by a factor of $2^2=4$, $2^3=8$ or $2^4=16$ thereby allowing this 60-electrode retinal prosthesis to be used to actuate 240, 480 or 960 electrodes.

The demultiplexer circuit of the present invention has its own dc power supply formed on the same semiconductor substrate so that no external dc voltages are needed to operate the demultiplexer circuit thereby avoiding any possibility for electrolysis.

The demultiplexer circuit of the present invention also provides electrostatic discharge protection to prevent damage of the demultiplexer circuit during implantation of the neural prosthesis or thereafter.

These and other advantages of the present invention will become evident to those skilled in the art.

SUMMARY OF THE INVENTION

The present invention relates to a demultiplexer circuit formed on a semiconductor substrate which comprises a power supply having an energy storage capacitor and a bridge rectifier both formed on the semiconductor substrate, with the power supply receiving an alternating-current (ac) input voltage to generate therefrom all of the direct-current (dc) electrical power to operate the demultiplexer circuit. The demultiplexer circuit also includes a plurality of latches and one or more $1:2^N$ demultiplexers formed on the semiconductor substrate. Each latch has an ac-coupled input wherein a digital addressing signal is received one bit at a time, with each bit of the digital addressing signal being stored in that latch and provided to an output thereof until such time as a subsequent bit of the digital addressing signal is received at the ac-coupled input of that latch. Each $1:2^N$ demultiplexer has a neural stimulation signal input and an integer number N of addressing inputs. The N addressing inputs are connected to the outputs of a set of N of the plurality of latches to receive N bits of the digital addressing signal stored in the set of N latches, with the N bits of the digital addressing signal being used to program that $1:2^N$ demultiplexer and thereby connect the neural stimulation signal input to one of $2^N$ outputs for that $1:2^N$ demultiplexer. The number N can be, for example, in a range of 2-4. A bi-phasic current signal can be provided to the neural stimulation signal input of each $1:2^N$ demultiplexer, with the output of each $1:2^N$ demultiplexer being connected to a neural stimulation electrode. This allows a neural stimulation signal provided at the input of each $1:2^N$ demultiplexer to be sequentially routed to the neural stimulation electrodes which are connected to the outputs of that $1:2^N$ demultiplexer.

The bridge rectifier can comprise a plurality of interconnected complementary metal-oxide semiconductor (CMOS) transistors.

The ac-coupled input to each latch can comprise a coupling capacitor formed from a plurality of metal layers which are stacked up with a dielectric layer separating each adjacent pair of the metal layers, and with one of the metal layers forming a bond pad for the ac-coupled input to that latch. As an example, the plurality of stacked metal layers can comprise three metal layers with an upper metal layer and a lower metal layer of the three metal layers being electrically connected together to form an input side of the coupling capacitor, and with an intermediate metal layer of the three metal layers being located between the upper metal layer and the lower metal layer to form an output side of the coupling capacitor.

Each latch can comprise a first pair of inverters which are connected in series with a feedback resistor connected between an input and an output of the first pair of inverters, and a second pair of inverters which are connected in series with the first pair of inverters to provide the output for that latch. Each latch can also include a reverse-biased diode connected between the input of the first pair of inverters and each power supply connection to that latch, and another reverse-biased diode connected between the output of the first pair of inverters and each power supply connection to that latch. A pair of diodes can also be connected in series between the ac-coupled input and the output of the first pair of inverters, with the pair of diodes being connected in a cathode-to-cathode configuration or in an anode-to-anode configuration. These diodes are provided in each latch to protect against an electrostatic discharge which could otherwise damage CMOS transistors which are used to form the latches and the remainder of the demultiplexer circuit.

Each $1:2^N$ demultiplexer can comprise a plurality of digital logic gates (e.g. NAND gates and inverters) having inputs of the N bits of the digital addressing signal and having outputs which are connected to N transmission gates, with the outputs of the digital logic gates being used to switch one of the N transmission gates to connect the neural stimulation signal input for that 1:$2^N$ demultiplexer to one of the $2^N$ outputs for that 1:$2^N$ demultiplexer.

The semiconductor substrate can comprise a bulk silicon substrate or a silicon-on-insulator (SOI) substrate. An SOI substrate has a monocrystalline silicon base and a monocrystalline silicon layer with an oxide layer being located between the monocrystalline silicon base and the monocrystalline silicon layer. The CMOS transistors are formed in the monocrystalline silicon layer which is also termed a device layer.

A plurality of electrical vias (i.e. electrical feedthroughs) can be formed through the semiconductor substrate, with the electrical vias being connected at one end thereof to the $2^N$ outputs of each 1:$2^N$ demultiplexer, and with an opposite end of each electrical via being electrically connectable to a neural stimulation electrode. This allows each input to the demultiplexer circuit to be located on a top side of the semiconductor substrate, with each output of the demultiplexer circuit being located on a bottom side of the semiconductor substrate. This simplifies connecting the demultiplexer circuit to an electrode array, and to a conventional neural implant device which provides the ac input voltage, and each digital addressing signal and neural stimulation signal.

The present invention also relates to a demultiplexer circuit for use with a neural stimulator. The demultiplexer circuit comprises a plurality of latches and a plurality of 1:$2^N$ demultiplexers formed on a semiconductor substrate together with a power supply which provides all of the dc voltages needed to operate the latches and demultiplexers. The number N can be an integer number in the range of 2 to 4 so that the 1:$2^N$ demultiplexers can be 1:4 demultiplexers, 1:8 demultiplexers, or 1:16 demultiplexers.

Each latch receives addressing information one bit at a time and stores that bit of the addressing information until such time as a subsequent bit of the addressing information is received from the neural stimulator. A neural stimulation signal and N bits of the addressing information from a set of N of the latches are provided to inputs of each 1:$2^N$ demultiplexer, with the neural stimulation signal input being connected to one of $2^N$ outputs of that 1:$2^N$ demultiplexer in response to the addressing information provided to that 1:$2^N$ demultiplexer. The $2^N$ outputs of each 1:$2^N$ demultiplexer are connected to separate neural stimulation electrodes so that the neural stimulation signal can be routed through each 1:$2^N$ demultiplexer to one of the neural stimulation electrodes at a particular instant in time. The neural stimulator can comprise, for example, at least a part of a retinal prosthesis; and the current signal can comprise a bi-phasic current signal.

The demultiplexer circuit can be formed on a bulk silicon substrate, or on a silicon-on-insulator (SOI) substrate. The SOI substrate comprises a monocrystalline silicon base and a monocrystalline silicon layer with an oxide layer sandwiched therebetween.

Electrical connections from the neural stimulator can be made to the demultiplexer circuit on a top side of the semiconductor substrate. Electrical connections from the outputs of the demultiplexer circuit to the neural stimulation electrodes, which can be located on a bottom side of the semiconductor substrate, can be made using electrical vias through the semiconductor substrate.

The power supply can comprise a bridge rectifier and an energy storage capacitor, with the bridge rectifier further comprising a plurality of interconnected complementary metal-oxide semiconductor (CMOS) transistors.

Each latch in the demultiplexer circuit can be formed with an alternating-current (ac)-coupled input wherein the addressing information for that latch is received. The ac-coupled input can comprise a coupling capacitor formed from two or more metal layers with a dielectric layer being sandwiched between each pair of the metal layers. An upper metal layer of the two or more metal layers can be used to form a bond pad for the ac-coupled input to that latch, thereby reducing the space on the semiconductor substrate which is required to form the ac-coupled input. Each latch can also comprise a plurality of diodes to provide electrostatic discharge protection for that latch.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
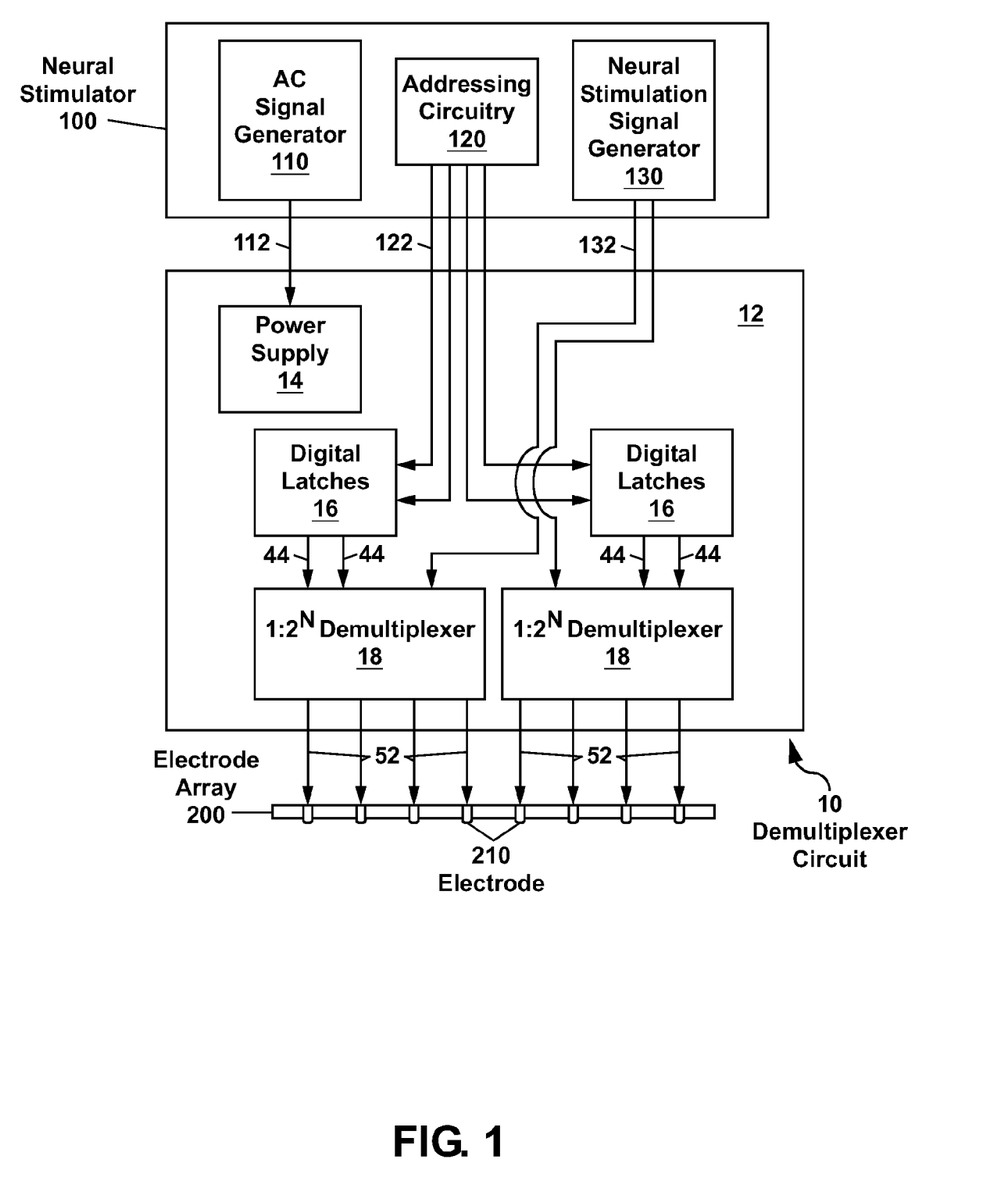
FIG. 1 shows a schematic diagram of a demultiplexer circuit formed according to the present invention together with a neural stimulator and an electrode array which can be used in conjunction with the demultiplexer circuit.

Referring to FIG. 1, there is shown a schematic diagram of the demultiplexer circuit 10 of the present invention. The demultiplexer circuit 10 in FIG. 1 comprises a semiconductor substrate 12 on which a power supply 14 is formed which provides all the direct-current (dc) electrical power which is needed to operate a plurality of digital latches 16 and one or more 1:$2^N$ demultiplexers 18 located on the same semiconductor substrate 12. The demultiplexer circuit 10 can be used with a conventional neural stimulator 100 and a neural electrode array 200 to increase the number of individual neural stimulation electrodes 210 which can be driven by the neural stimulator 100.

In FIG. 1, the neural stimulator 100 can comprise an alternating current (ac) signal generator 110 together with digital addressing circuitry 120 and a neural stimulation signal generator 130. The ac signal generator 110 can provide an ac input voltage 112 to the power supply 14 which can be up to several tens of volts with a frequency which can be up to about 10 kiloHertz (kHz). The ac input voltage 112 can be sinusoidal or square-wave or can have any arbitrary shape. However, the ac input voltage 12 must not include any dc component when the ac input voltage 112 is conducted through wiring to the power supply 14 since the wiring may become exposed to body fluids, and this can lead to electrolysis and to corrosion of the wiring.

In the demultiplexer circuit 10 of the present invention, all of the dc voltages which are needed to operate the demultiplexer circuit 10 are generated directly on the semiconductor substrate 12 which can be sealed within a biocompatible hermetic enclosure to provide protection against any electrolysis and corrosion. These dc voltages +V and −V, which can be, for example, in the range of ±7 to ±8 Volts, are generated by the power supply 14 which is formed on the semiconductor substrate 12.

Figure 2:
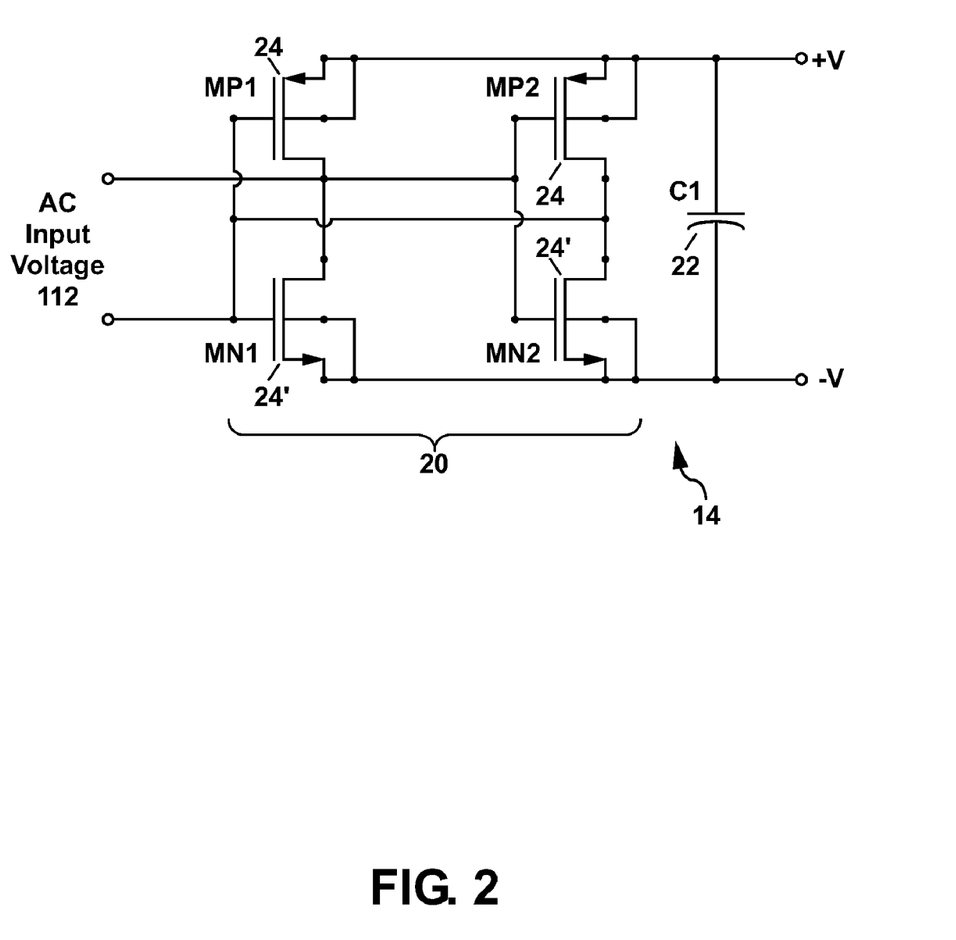
FIG. 2 shows a schematic circuit diagram for a power supply which is used in the demultiplexer circuit of FIG. 1, with the power supply being located on the same semiconductor substrate as the remainder of the demultiplexer circuit.

The power supply 14 comprises a bridge rectifier 20 formed from a pair of p-channel CMOS transistors 24 and a pair of n-channel CMOS transistors 24' connected as shown in the schematic circuit of FIG. 2. In FIG. 2, the pair of p-channel CMOS transistors 24 are labelled as "MP1" and "MP2;" and the pair of n-channel CMOS transistors 24' are labelled as "MN1" and "MN2." The CMOS transistors 24 and 24' in the power supply 14 and in the remainder of the demultiplexer circuit 10 can be formed using standard integrated circuit (IC) processes which have been adapted to provide transistors 24 and 24' which operate at voltages up to the maximum ac input voltage 112 (e.g. 20-25 volts).

The power supply also includes an energy storage capacitor 22, which is labelled as "C1" in FIG. 2, and which can have a capacitance of, for example, 300 picoFarads (pF). The dc electrical current provided by the power supply 14 can be up to a few hundred microAmps (μA).

The demultiplexer circuit 10 includes a plurality of latches 16 which are addressed using information which can be provided by addressing circuitry 120 located in the conventional neural stimulator 100 as shown in FIG. 1. The addressing information can be provided as a plurality of digital addressing signals 122. In other embodiments of the present invention, the digital addressing signals 122 can be generated by a computer, microprocessor or sensory signal processor. The addressing information used to generate the digital addressing signals 122 can come from a sensory device which is not shown in FIG. 1. In the case of a visual prosthesis, the sensory device can be a video camera, CCD camera, digital camera, etc.

In FIG. 1, one of the digital addressing signals 122 is provided to each latch 16 and is stored therein one bit at a time for use in programming the 1:$2^N$ demultiplexer 18 which is connected to that latch 16. When each demultiplexer 18 comprises a 1:4 demultiplexer 18, then two latches 16 are required to receive and store the two bits of addressing information needed to program each 1:4 demultiplexer 18. These two bits of the addressing information are provided by two digital addressing signals 122, with each addressing signal 122 being provided to an ac-coupled input 26 (see FIG. 3A) of one of the two latches 16. In general, a set of N latches 16 will be needed for programming each 1:$2^N$ demultiplexer 18 where N is an integer which is generally in a range of 2-4. A separate digital addressing signal 122 is provided to the ac-coupled input 26 of each latch 16 in the set of N latches 16 associated with each 1:$2^N$ demultiplexer 18.

Figure 3A:
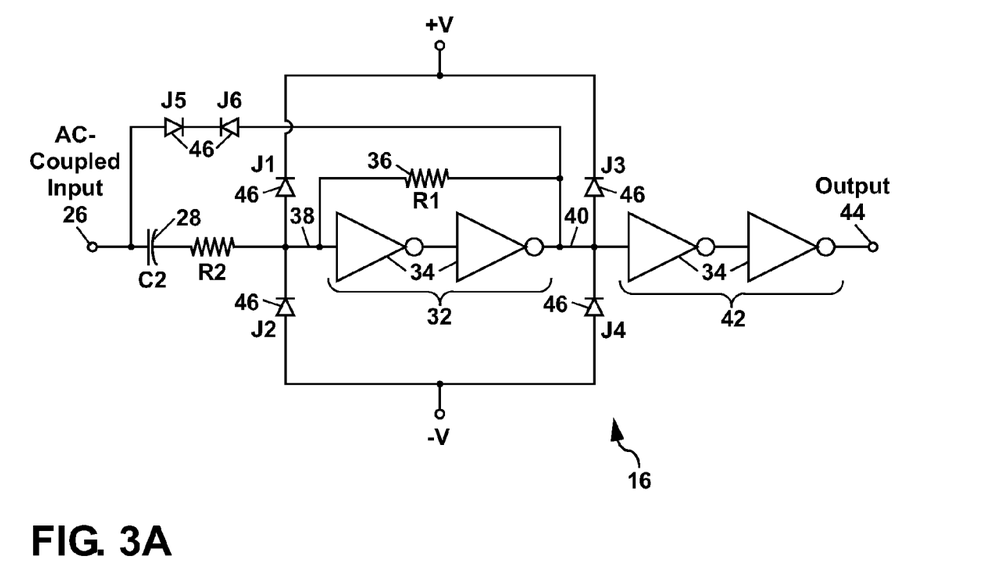
FIG. 3A shows a schematic circuit diagram for a digital latch which is used in the demultiplexer circuit of FIG. 1.

FIG. 3A shows an example of a schematic circuit which can be used for each latch 16. In FIG. 3, the ac-coupled input 26 comprises a coupling capacitor 28 which is labelled as "C2." This coupling capacitor 28 can have a capacitance of, for example, 10 pF and can be formed integrally with a bond pad on the semiconductor substrate 12 as will be described in more detail hereinafter. The coupling capacitor 28 is used to ensure that the digital addressing signals 122 do not have any dc signal component which might otherwise arise due to a difference in electrical potential between the neural stimulator 100 and the demultiplexer circuit 10. With all the signals coupled into and out of the demultiplexer circuit 10 being ac signals, no electrical ground connection is provided to the demultiplexer circuit 10 from the neural stimulator 100, or from any other source. This also ensures that no dc signals are externally coupled into the demultiplexer circuit 10 to prevent the possibility of electrolysis or corrosion during long-term use of the apparatus 10.

Each latch 16 is formed from a first pair 32 of CMOS inverters 34 which are connected in series with a feedback resistor 36, which is labelled as "R1" in FIG. 3A, being connected between an input 38 and an output 40 for the first pair 32 of the CMOS inverters 34. The resistance of the feedback resistor 36 can be, for example, 200 kiloOhms (kΩ). Another resistor labelled "R2" in FIG. 3A can be used at the input 38 of the first inverter pair 32, with the resistor R2 having a resistance of, for example, 500 Ω.

Figure 3B:
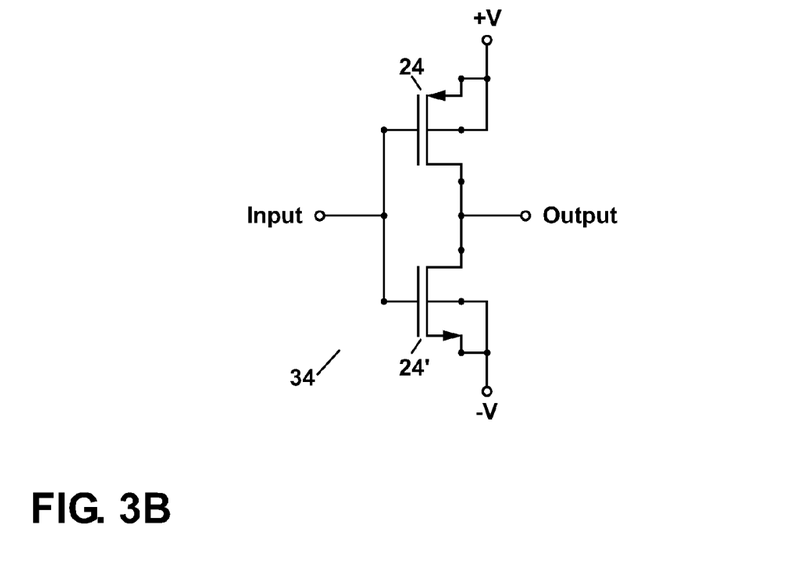
FIG. 3B shows a schematic circuit diagram for an inverter which is used in the digital latch of FIG. 3A.

Each latch 16 also includes a second pair 42 of CMOS inverters 34 which are connected in series to the output 40 but without any feedback resistor. This second pair 42 of the CMOS inverters 34 acts as a buffer to provide the logic state of the latch 16 to a latch output 44. Each CMOS inverter 34 is a NOT logic gate and can be formed from a p-channel CMOS transistor 24 interconnected to an n-channel CMOS transistor 24' as shown in FIG. 3B.

The first pair 32 of the CMOS inverters 34 in each latch 16 receives one bit at a time of the digital addressing signal 122 provided to the ac-coupled input 26 of that latch 16 and brings the signal level for each bit up to a digital-logic-state level corresponding to one of the power supply voltages (e.g. about +V for bit having a logical "1" state bit and about −V for a bit having a logical "0" state, or vice versa). The first pair 32 of the CMOS inverters 34 then stores that bit until such time as a subsequent bit of the digital addressing signal 122 is received by that latch 16. At this time, the subsequent bit of the digital addressing signal 122 changes the logic state of the latch 16, as needed, with the subsequent bit of the addressing signal 122 now being stored in the latch 16 and provided to the latch output 44. In this way, the digital addressing signal 122 provided to each set of N latches 16 acts as a clock to control the operation of those latches 16 and the 1:$2^N$ demultiplexer 18 which is connected thereto.

In other embodiments of the present invention, a portion of the ac input voltage 112 can be input to one of the latches 16 to generate a clock which can then be used to clock the operation of each demultiplexer circuit 10.

The CMOS transistors 24 and 24' in the demultiplexer circuit 10 can be damaged by electrostatic discharges which can occur during surgical procedures used to install a neural implant containing the demultiplexer circuit 10 or thereafter during use of the demultiplexer circuit 10. Therefore, electrostatic discharge protection is provided in the latches 16 to protect the demultiplexer circuit 10 of the present invention. This is done by using a plurality of diodes 46 which are reverse-biased by the power supply voltages +V and −V during normal operation of the latch 16 (i.e. in the absence of any electrostatic discharge at the input 38 or the output 40 of the first pair 32 of the inverters 34). These diodes 46 are labelled as "J1" through "J4" in FIG. 3A. The diodes J1 and J2 are connected between the input 38 of the first pair 32 of the inverters 34 and each power supply connection (i.e. the connections to the power supply voltages +V and −V) for the latch 16; and the diodes J3 and J4 are connected between the output 40 of the first pair 32 of the inverters 34 and each power supply connection. These diodes J1 through J4 conduct any electrostatic discharge away from the input 38 or output 40 to the power supply connections and therefrom to the energy storage capacitor C1 (see FIG. 2) where the electrostatic discharge is dissipated. Any positive electrostatic discharge which appears at the input 38 or output 40 of the latch 16 and exceeds the power supply voltage +V will turn on diodes J1 or J3, respectively, so that the discharge is conducted through the diodes J1 or J3 to the +V power supply connection; whereas, any negative electrostatic discharge at the input 38 or output 40 which exceeds the power supply voltage −V will turn on diodes J2 or J4, respectively, to conduct the discharge through the diodes J2 or J4 to the −V power supply connection.

Additional diodes 46 can be provided in between the ac-coupled input 26 and the output 40 for the first pair 32 of the inverters 34 as shown in FIG. 3A. These additional diodes 46, which are labelled "J5" and "J6" in FIG. 3A, are connected in series with an opposite polarity (e.g. connected in a cathode-to-cathode configuration as shown in FIG. 3A, or connected in an anode-to-anode configuration). Any electrostatic discharge, which exceeds a reverse-breakdown voltage of the diodes J5 and J6 will bypass the input 38 and be conducted through the diodes J5 and J6 to the output 40 and therefrom through the diodes J3 or J4 to the power supply connections +V or −V and therefrom to the energy storage capacitor C1 where the electrostatic discharge can be harmlessly dissipated.

The output 44 for each latch 16 provides each bit of the addressing information in turn to the $1:2^N$ demultiplexer 18 which is connected to the set of N latches 16 which are used to program that $1:2^N$ demultiplexer 18. This addressing information is then used by the $1:2^N$ demultiplexer 18 to control a plurality of transmission gates 58 which route the neural stimulation signal 132 through the $1:2^N$ demultiplexer 18 to a particular electrode 210 which is determined by the addressing information. Each sequential bit of the addressing information can be used to control the $1:2^N$ demultiplexer 18 and thereby re-route the neural stimulation signal 132 as needed to different electrodes 210 in the electrode array 200. Each $1:2^N$ demultiplexer 18 can be used to address a different set of $2^N$ electrodes 210.

Figure 4:
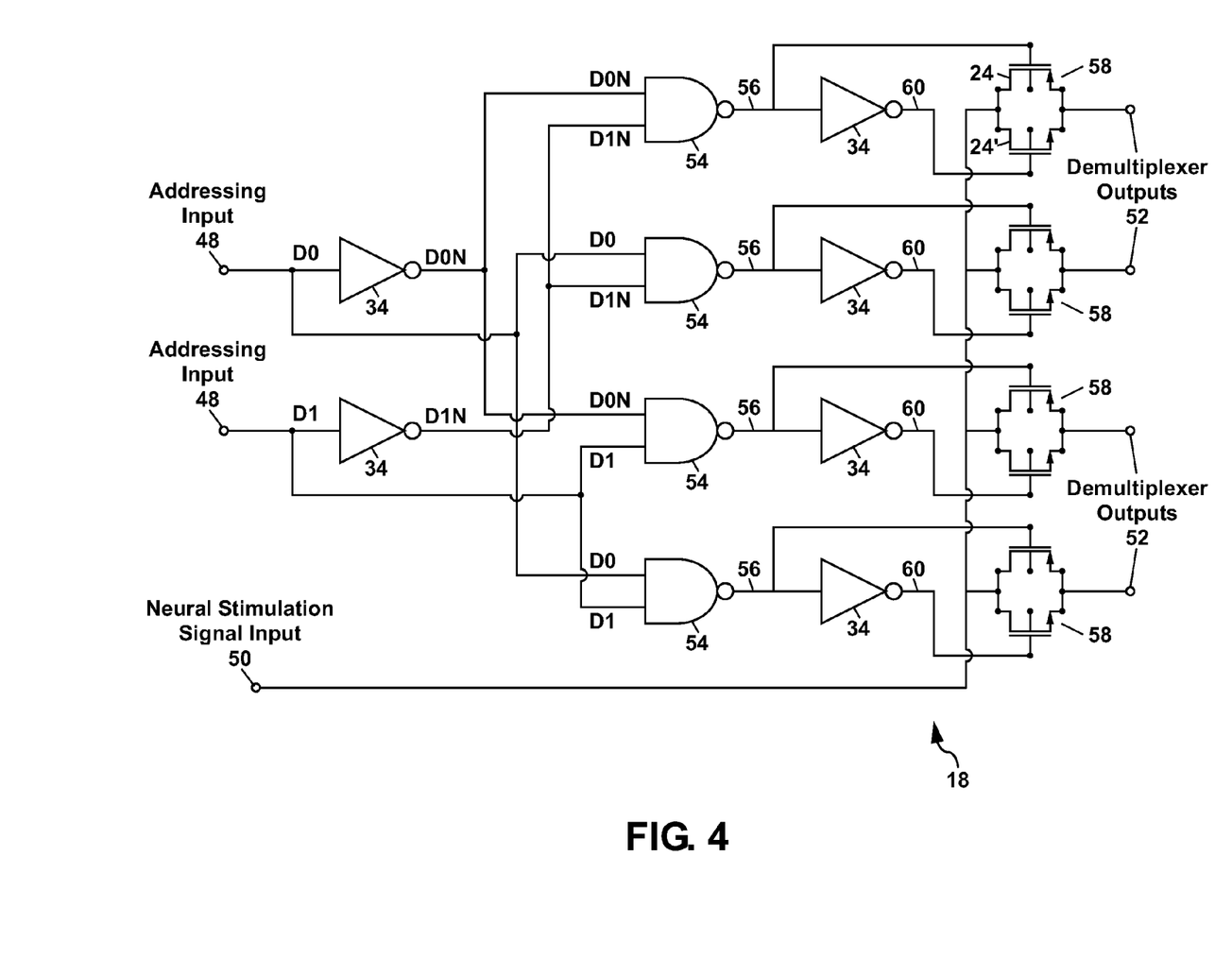
FIG. 4 shows a schematic circuit diagram for a 1:4 demultiplexer which can be used in the demultiplexer circuit of FIG. 1.

FIG. 4 shows an example of a $1:2^N$ demultiplexer 18 with N=2 (i.e. a 1:4 demultiplexer 18). In this example, the outputs 44 from a set of two digital latches 16 are connected to two addressing inputs 48 in the 1:4 demultiplexer to provide two bits of addressing information labelled "D0" and "D1" to the 1:4 demultiplexer 18. The bit "D0" can represent a least significant bit of an addressing information; and the bit "D1" can represent a most significant bit of the addressing information.

A neural stimulation signal 132 from the neural stimulation signal generator 130 in the neural stimulator 100 (see FIG. 1) can be connected to a neural stimulation signal input 50 of the 1:4 demultiplexer 18 as shown in FIG. 4. The 1:4 demultiplexer 50 then routes the neural stimulation signal 132 to one of four outputs 52 of the 1:4 demultiplexer 50 using the addressing information "D0" and "D1" so that the neural stimulation signal 132 can be provided to one of four different electrodes 210 which are connected to the 1:4 demultiplexer 18. As the addressing information changes over time, the electrode 210 selected to receive the neural stimulation signal 132 will also change accordingly.

Although only one electrode 210 receives the neural stimulation signal 132 at any given instant in time, the 1:4 demultiplexer 18 in FIG. 4 can be clocked by the addressing information at a rate which is much faster than a neural response time so that up to all four of the electrodes 210 connected to the outputs 52 of the 1:4 demultiplexer 18 can effectively act to stimulate four different areas of neural tissue. As an example, with the addressing information being provided to the 1:4 demultiplexer 18 at a data rate of 120 bits per second for each digital addressing signal 122, the 1:4 demultiplexer 18 can be used to provide the outputs 52 to four different electrodes 210, with each electrode 210 being addressed 30 times per second. When used in a retinal implant, this addressing speed of 30 times per second should be sufficiently fast to provide the perception of continuous vision in four different retinal areas being stimulated by the four electrodes 210. The use of a higher data rate for each digital addressing signal 122 will allow the electrodes 210 connected to each 1:4 demultiplexer 18 to be activated at a correspondingly higher rate since the demultiplexer circuit 10 of the present invention is not limited to operation at a data rate of 120 bits per second, but can operate at data rates up to several tens of kiloHertz. Thus, increasing the data rate for each digital addressing signal 122 to 240 bits per second will allow addressing of each electrode 210 at 60 times per second using a plurality of 1:4 demultiplexers 18.

For use with a retinal implant neural stimulator 100, the exact number of $1:2^N$ demultiplexers 18 and sets of digital latches 16 would correspond to the number of neural stimulation signals 132 provided by the neural stimulator 100. Thus, for example, when the neural stimulator 100 provides sixty neural stimulation signals 132, the demultiplexer circuit 10 of FIG. 1 can contain sixty different 1:4 demultiplexers formed according to FIG. 4 for use with an electrode array 200 comprising 240 individual electrodes 210. In other embodiments of the present invention, a plurality of 1:8 or 1:16 demultiplexers 18 can be formed in a manner similar to that shown in FIG. 4 except for an increased number of addressing inputs 48 and logic gates (i.e. inverters, NAND gates, and transmission gates) which are scaled accordingly. When a plurality of 1:8 or 1:16 demultiplexers 18 are used in the demultiplexer circuit 10 to address a larger number of electrodes 210 in an array 200 (e.g. 480 electrodes 210 using sixty 1:8 demultiplexers 18, or 960 electrodes 210 using sixty 1:16 demultiplexers 18), the data rate for each digital addressing signal 122 can be increased, as needed, to maintain a predetermined electrode activation rate to provide for continuous vision.

In the example of FIG. 4, the 1:4 demultiplexer 18 comprises a pair of inverters 34 which receive the addressing inputs 48 and generate therefrom a complementary bit "D0N" of the bit "D0" and a complementary bit "D1N" of the bit "D1." Thus, when "D0" is in a "0" logic state, then "D0N" is in a "1" logic state; and when "D0" is in a "1" logic state, then "D0N" is in a "0" logic state. Various combinations of the bits "D0," "D0N," "D1," and "D1N" are then provided to a plurality of NAND gates 54 in the 1:4 demultiplexer 18, with the number of inputs to each NAND gate 54 being, in general, equal to the integer N, which is also the number of the addressing inputs 48, and with the number of NAND gates 54 in each 1:$2^N$ demultiplexer 18 being equal to $2^N$. Thus, in the example of FIG. 4, the 1:4 demultiplexer 18 requires four NAND gates 54, with each NAND gate 54 having two inputs and receiving a different combination of the bits "D0," "D0N," "D1," and "D1N."

In FIG. 4, each NAND gate 54 generates a NAND function output 56 which is provided to a gate electrode of a p-channel CMOS transistor 24 in a transmission gate 58. A complement 60 of the NAND function output 56 is generated by an inverter 34 following each NAND gate 54 with the complement 60 being provided to the gate electrode of an n-channel CMOS transistor 24' in the same transmission gate 58. Each transmission gate 58 also includes a signal input which is connected to the neural stimulation signal input 50 and a signal output which forms one of the $2^N$ demultiplexer outputs 52 as shown in FIG. 4.

The NAND function output 56 and complement 60, which are provided to each transmission gate 58, switch that transmission gate 58 "on" or "off" depending upon the logic states of the inputs to the NAND gate 54 driving that transmission gate 58. When a particular transmission gate 58 is switched "on," the neural stimulation signal 132 provided to the input 50 of the 1:$2^N$ demultiplexer 18 is routed through that transmission gate 58 to the demultiplexer output 52 and to the electrode 210 which is connected to that output 52. During this time, the remaining transmission gates 58 are switched "off" so that the neural stimulation signal 132 is blocked from reaching the remainder of the outputs 52 and electrodes 210 connected thereto.

Figure 5:
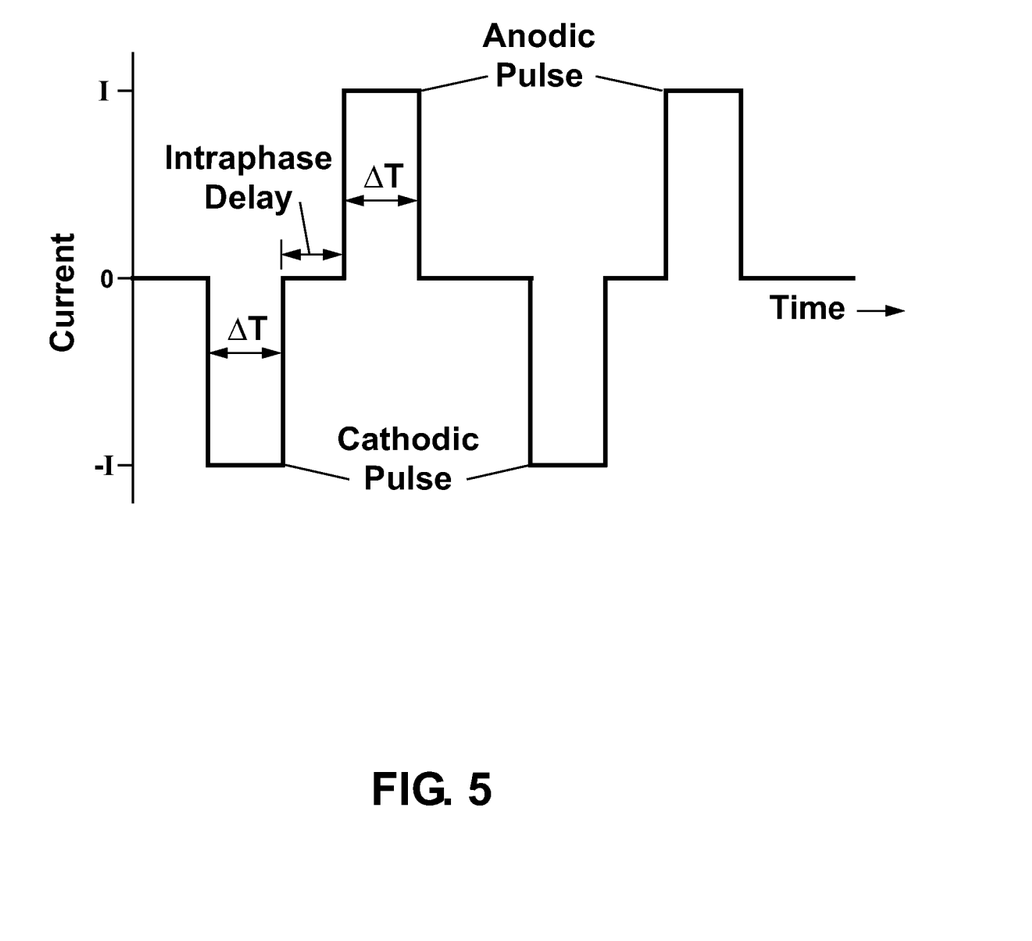
FIG. 5 shows a portion of a bi-phasic current signal which can be provided as a neural stimulation signal input to the demultiplexer circuit of FIG. 1, with the bi-phasic current signal comprising alternating cathodic and anodic current pulses separated by an intraphase delay.

The neural stimulation signal 132 can be a bi-phasic current signal having periodic cathodic and anodic current pulses separated by an intraphase delay, with the cathodic and anodic current pulses generally having substantially the same magnitude I and substantially the same time duration $\Delta t$. The ordering of the cathodic and anodic current pulses can, in some instances, be reversed. FIG. 5 shows a portion of such a bi-phasic current signal with a cathodic current pulse being followed by an anodic current pulse, and with this arrangement of pulses being periodically repeated. The use of a bi-phasic neural stimulation signal 132 is advantageous to prevent any net charge accumulation on the electrodes 210 and thereby prevent any corrosion and gas formation at the electrodes 210. In the bi-phasic neural stimulation signal 132, the time duration for each cathodic current pulse and each anodic current pulse can be, for example, about one millisecond or less; and the magnitude of each current pulse can be up to a few hundred microAmps (e.g. 700 $\mu A$).

When the demultiplexer circuit 10 of the present invention is used in a retinal prosthesis, the bi-phasic current signal can be generated, for example, using intensity information from a pixelized image of a scene detected by a video camera. The pixelized image can be divided into sets of $2^N$ pixels, with the location and timing of each pixel a particular set of the $2^N$ pixels being encoded by the addressing circuitry 120 to generate the addressing information for that set of the $2^N$ pixels, and with the light intensity for the individual pixels in that set of the $2^N$ pixels being encoded and provided to the neural stimulation signal generator 130 to generate a stream of bi-phasic current pulses (i.e. the bi-phasic current signal 132) with the appropriate magnitude (i.e. intensity) and timing. Each 1:$2^N$ demultiplexer 18 in the demultiplexer circuit 10 then receives the addressing information for a particular set of the $2^N$ pixels and uses the addressing information to demultiplex the stream of bi-phasic current pulses and to provide the individual bi-phasic current pulses to specific electrodes 210 in the array 200 to stimulate nearby retinal cells and thereby generate a perceived pattern of spots of light (i.e. phosphenes) which simulates that set of the $2^N$ pixels of the scene.

Figure 6:
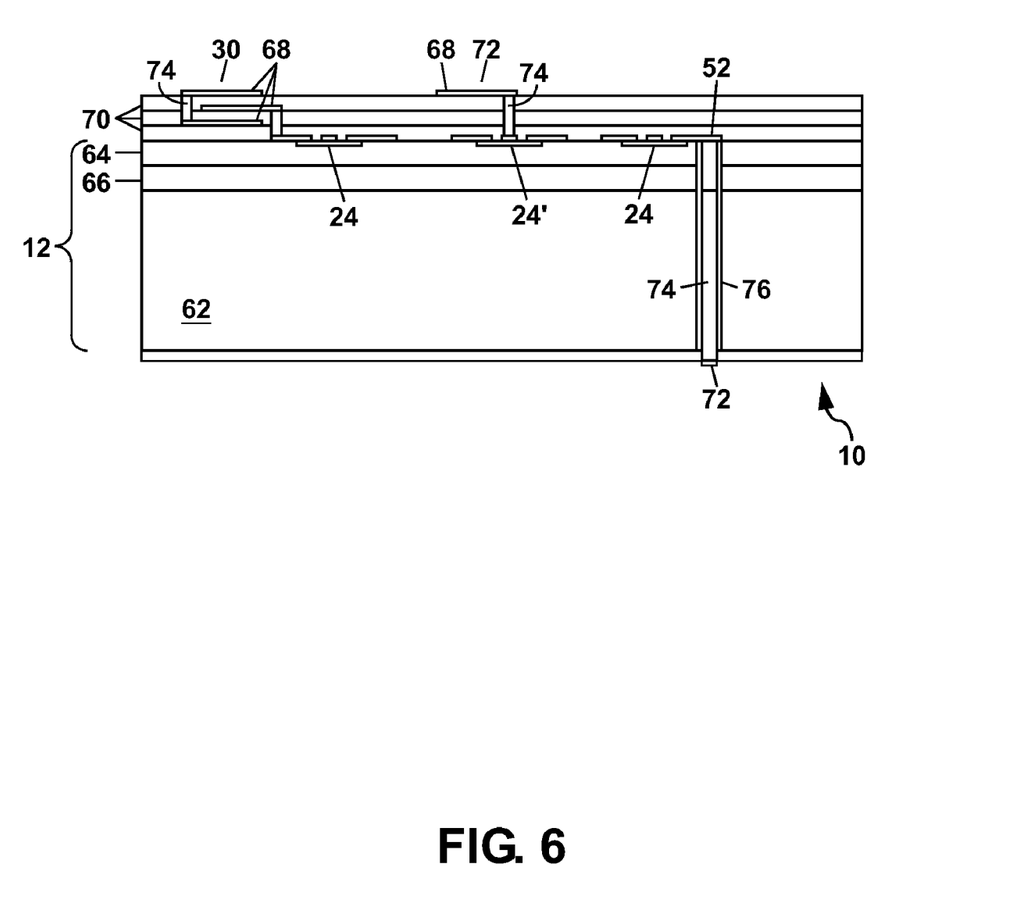
FIG. 6 schematically illustrates in cross-section view a portion of a silicon-on-insulator (SOI) substrate to show details of the demultiplexer circuit, including the coupling capacitor, the CMOS transistors, the single-level and multi-level bond pads, and electrical vias.

The semiconductor substrate 12 on which the demultiplexer circuit 10 is formed can comprise either a bulk silicon substrate, or a silicon-on-insulator (SOI) substrate. FIG. 6 schematically illustrates in cross-section view an SOI substrate 12 to show how the various inputs and outputs can be provided to and from the demultiplexer circuit 10, and to show details of the coupling capacitor 28 which is formed integrally with the multi-level bond pad 30. In FIG. 6, the SOI substrate 12, which can be procured commercially, comprises a monocrystalline silicon base 62 and a monocrystalline silicon layer 64 (also termed a device layer) with an oxide layer 66 being located between the monocrystalline silicon base 62 and the monocrystalline silicon layer 64. The p-channel CMOS transistors 24 and the n-channel CMOS transistors 24' are formed in the monocrystalline silicon layer 64 using a series of well-known semiconductor IC processing steps (e.g. 0.5 $\mu m$ CMOS 3-layer-metal technology operating at voltages up to about 20-25 volts).

Two or more layers of a deposited and patterned metal 68 can be used to interconnect the CMOS transistors 24 and 24', with the metal layers 68 being separated by electrically-insulating dielectric layers 70 which can comprise, for example, silicon dioxide or a silicate glass such as tetraethylortho silicate (TEOS). To form each coupling capacitor 28, a plurality of the metal layers 68 can be stacked up (i.e. superposed) with one of the dielectric layers 70 separating each adjacent pair of the stacked metal layers 68. The lateral dimensions of each metal layer 68 which forms the coupling capacitor 28 can be, for example, about 300 $\mu m$.

When two metal layers 68 are used to form the coupling capacitor 28 in each digital latch 16, one of the metal layers 68 can form a single-level bond pad 72 and an input side of the capacitor 28, with the other metal layer 68 forming an output side of the capacitor 28 and being connected to the resistor R2. When three metal layers 68 are used to form the coupling capacitor 28 in each digital latch 16, an upper metal layer and a lower metal layer of the three metal layers 68 can be electrically connected together by an electrical via 74 to form the input side of the capacitor 28, and an intermediate metal layer of the three metal layers 68 located between the upper metal layer and the lower metal layer can form the output side of the capacitor 28. This is schematically illustrated in the cross-section view of FIG. 6. In this latter case, and the upper metal layer and the lower metal layer also form a multi-level bond pad 30.

It should be noted that FIG. 6 is not intended to show a cross-section of the entire demultiplexer circuit 10, but merely to show certain details of the demultiplexer circuit 10 beyond those provided in FIGS. 1-5 to aid in understanding fabrication of the demultiplexer circuit 10 of the present invention. Additionally, although FIG. 6 shows an SOI substrate 12, the elements including the transistors 24 and 24', the coupling capacitor 28, and the electrical vias 74 shown in FIG. 6 can also be similarly fabricated on a bulk silicon substrate 12. Forming the coupling capacitors 28 integrally with the bond pads 30 or 72 is advantageous to save space on the semiconductor substrate 12 since there can be up to hundreds or more individual latches in the demultiplexer circuit 10 with each latch 16 requiring its own coupling capacitor 28 and bond pad 30 or 72.

In FIG. 6, additional single-level bond pads 72 can be formed from the upper metal layer 68 on a top side of the SOI substrate 12, and from an additional deposited and patterned metal layer located on a bottom side of the SOI substrate 12.

The single-level bond pads 72 on the top side of the SOI substrate, which can have lateral dimensions of, for example, 100 μm, can be used to provide electrical connections for the ac input voltage 112 and the neural stimulation signals 132. The single-level bond pads 72 on the bottom side of the SOI substrate 12 can provide electrical connections from the demultiplexer outputs 52 to the electrodes 210 using a plurality of electrical vias 72 which are formed through the SOI substrate 12. These vias 72 can comprise a lower portion formed from the monocrystalline silicon base 62, which can be doped for electrical conductivity, and an upper portion of each via 72 can comprise deposited metal or doped polycrystalline silicon (also termed polysilicon). An annular opening, which is formed about the vias 72 by deep reactive ion etching (DRIE), can be filled with an electrically-insulating material 76 which can comprise a commercially-available polymer underfill material which can be wicked into the annular opening by capillary forces. Each via 74 through the SOI substrate 12 can be, for example, about 100 μm in diameter with a separation between adjacent vias 74 being, for example, 300 μm.

Although the electrical vias 74 have been described above as being formed in an SOI substrate 12, those skilled in the art will understand that the vias 74 can be similarly formed in a bulk semiconductor substrate 12 for embodiments of the demultiplexer circuit 10 which are formed on such a bulk semiconductor substrate 12.

Figure 7A:
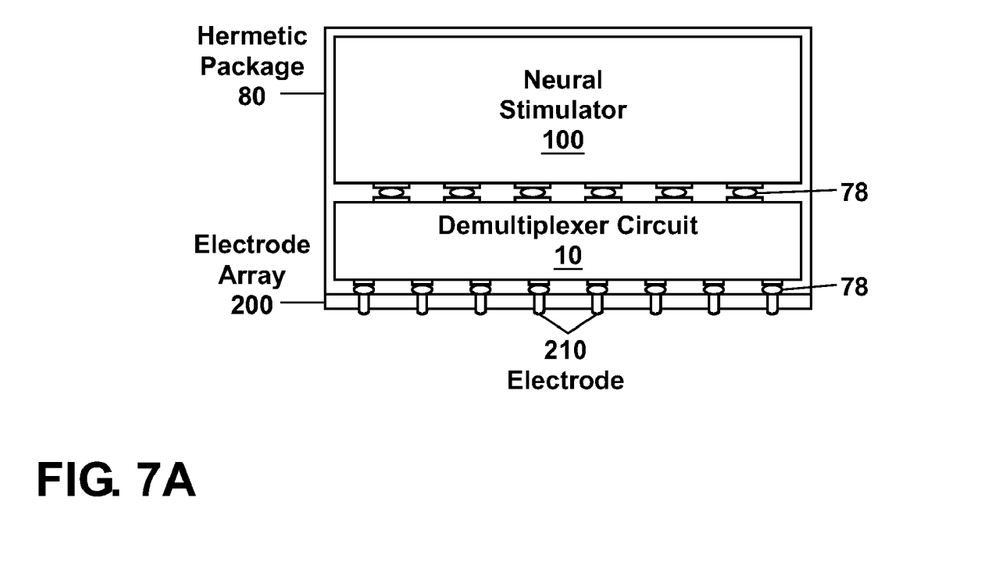
FIG. 7A schematically illustrates the demultiplexer circuit 10 of FIG. 1 packaged together with the neural stimulator and electrode array shown in FIG. 1.

By forming the demultiplexer circuit 10 on a double-sided semiconductor substrate 12 as shown in the example of FIG. 6, the neural stimulator 100 can be connected to the top side of the substrate 12 containing all of the inputs to the demultiplexer circuit 10 using an anisotropic conductive film, an electrically-conductive adhesive (e.g. a conductive epoxy), or a plurality of solder ball bonds 78 (also termed bump bonds) which are shown in the schematic cross-section view of FIG. 7A. The electrode array 200 can be similarly connected to the bottom side of the substrate 12 using an additional anisotropic conductive film, or alternately an electrically-conductive adhesive or solder ball bonds. The demultiplexer circuit 10 and the neural stimulator 100 can then placed in a hermetically-sealed package 80 which, in some cases, can include the electrode array 200 formed in a wall of the package 80 (see e.g. U.S. patent application Ser. No. 11/588,905 which is incorporated herein by reference).

Packaging the neural stimulator 100 and the demultiplexer circuit 10 in the same package 80 is useful, for example, for implantation into a body (e.g. an eye) with the addressing information being transmitted inductively using send and receive coils or through wiring. The addressing information can be generated using a computer or microprocessor which is located external to the body.

The hermetically-sealed package 80 can comprise, for example, a ceramic package as disclosed in U.S. patent application Ser. No. 11/588,905. Alternately, the hermetically-sealed package 80 can comprise one or more layers of a biologically-inert material such as polycrystalline diamond, ultra-nanocrystalline diamond, polyimide or parylene which is conformally deposited over exposed surfaces of the demultiplexer circuit 10 and the neural stimulator 100. The biologically-inert material can also be deposited over the electrode array 200, if needed, with openings being formed through the biologically-inert material at the locations of the electrodes 210.

Figure 7B:
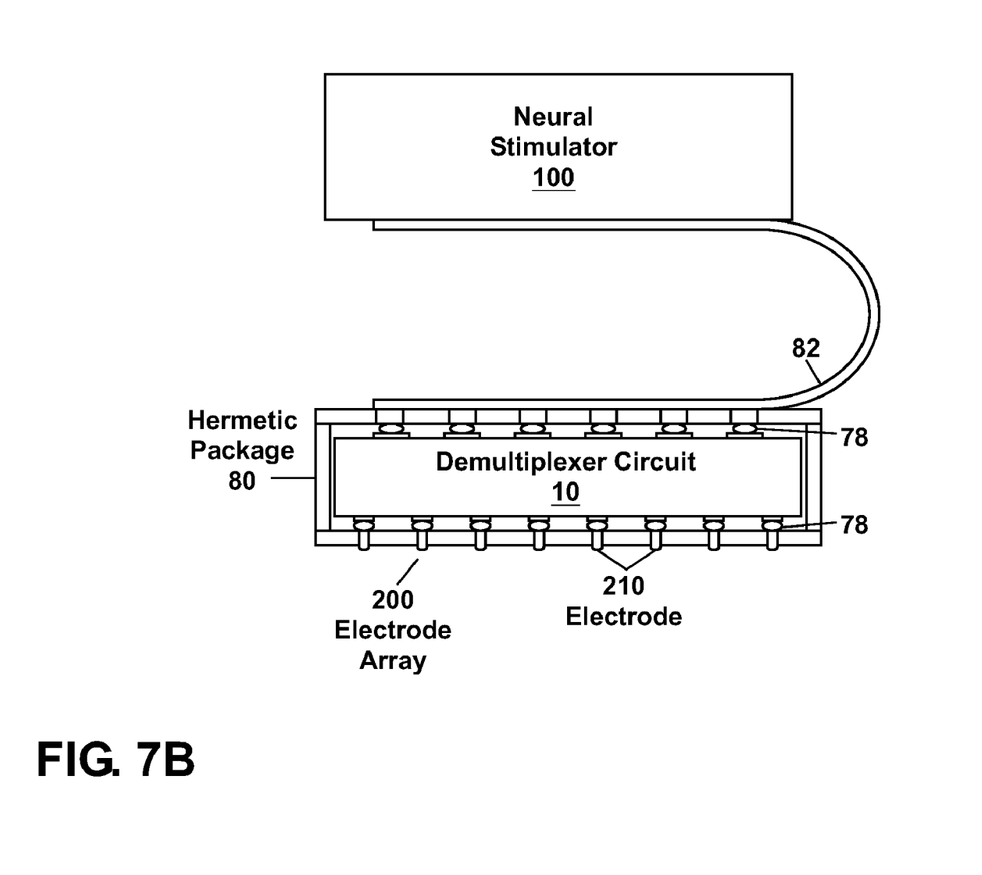
FIG. 7B schematically illustrates the demultiplexer circuit 10 of FIG. 1 packaged together with the electrode array shown in FIG. 1 and connected to the neural stimulator by a ribbon cable.

In other embodiments of the present invention, the demultiplexer circuit 10 can be located in a hermetically-sealed package 80 containing the electrode array 200; and the neural stimulator 100 can be connected to the demultiplexer circuit 10 using a ribbon cable 82. This is schematically illustrated in the cross-section view of FIG. 7B.

Packaging of the demultiplexer circuit 10 separate from the neural stimulator 100 is useful, for example, when the neural stimulator 100 is to be located outside of a body with the hermetic package 80 containing the demultiplexer circuit 10 and electrode array 200 being implanted within the body. Locating the neural stimulator 100 outside of the body reduces the effect of heating from the neural stimulator 100 on sensitive nerve cells, and also reduces the size of the package 80 which is implanted into the body. Additionally, the use of the demultiplexer circuit 10 can substantially reduce the size of the ribbon cable 82 which is required to connect the neural stimulator 100 to the demultiplexer circuit 10.

In yet other embodiments of the present invention, the electrode array 200 can be located at a distance from the demultiplexer circuit 10 and connected to the demultiplexer circuit 10 using a ribbon cable 82.

The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A demultiplexer circuit formed on a semiconductor substrate, comprising:
   a power supply having an energy storage capacitor and a bridge rectifier both formed on the semiconductor substrate, with the power supply receiving an alternating-current (ac) input voltage to generate therefrom all direct-current (dc) electrical power to operate the demultiplexer circuit;
   a plurality of latches formed on the semiconductor substrate, with each latch having an ac-coupled input wherein a digital addressing signal is received one bit at a time, with each bit of the digital addressing signal being stored in that latch and provided to an output thereof until such time as a subsequent bit of the digital addressing signal is received at the ac-coupled input of that latch, the ac-coupled input to each latch:
   including a coupling capacitor formed from a plurality of metal layers which are stacked up with a dielectric layer separating each adjacent pair of the metal layers; and
   one of the plurality of metal layers forming a bond pad for the ac-coupled input to that latch; and
   at least one 1:2 N demultiplexer formed on the semiconductor substrate, with each 1:2 N demultiplexer having a neural stimulation signal input and an integer number N of addressing inputs, and with the N addressing inputs being connected to the outputs of a set of N of the plurality of latches to receive N bits of the digital addressing signal stored in the set of N latches to program that 1:2 N demultiplexer and thereby connect the neural stimulation signal input to one of 2N outputs for that 1:2 N demultiplexer.

2. The demultiplexer circuit of claim 1 wherein a bi-phasic current signal is provided to the neural stimulation signal input of the at least one 1:2 N demultiplexer, and each output of the at least one 1:2 N demultiplexer is connected to a neural stimulation electrode.

3. The demultiplexer circuit of claim 1 wherein the bridge rectifier comprises a plurality of interconnected complementary metal-oxide semiconductor (CMOS) transistors.

4. The demultiplexer circuit of claim 1 where N is an integer number in the range of 2 to 4.

5. The demultiplexer circuit of claim 1 wherein the plurality of stacked metal layers comprises three metal layers with an upper metal layer and a lower metal layer of the three metal layers being electrically connected together to form an input side of the coupling capacitor, and with an intermediate metal layer of the three metal layers being located between the upper metal layer and the lower metal layer to form an output side of the coupling capacitor.

6. The demultiplexer circuit of claim 1 wherein a plurality of electrical vias are formed through the semiconductor substrate, with the electrical vias being connected at one end thereof to the 2N outputs of the at least one 1:2 N demultiplexer, and with an opposite end of each electrical via being electrically connectable to a neural stimulation electrode.

7. The demultiplexer circuit of claim 1 wherein each 1:2 N demultiplexer comprises a plurality of digital logic gates having inputs of the N bits of the digital addressing signal and having outputs which are connected to N transmission gates, with the outputs of the digital logic gates being used to switch one of the N transmission gates to connect the neural stimulation signal input for that 1:2 N demultiplexer to one of the 2N outputs for that 1:2 N demultiplexer.

8. A demultiplexer circuit formed on a semiconductor substrate, comprising:
  a power supply having an energy storage capacitor and a bridge rectifier both formed on the semiconductor substrate, with the power supply receiving an alternating-current (ac) input voltage to generate therefrom all direct-current (dc) electrical power to operate the demultiplexer circuit;
  a plurality of latches formed on the semiconductor substrate, with each latch having an ac-coupled input wherein a digital addressing signal is received one bit at a time, with each bit of the digital addressing signal being stored in that latch and provided to an output thereof until such time as a subsequent bit of the digital addressing signal is received at the ac-coupled input of that latch, each latch includes:
    a reverse-biased diode connected between the input of the first pair of inverters and each power supply connection to that latch; and
    another reverse-biased diode connected between the output of the first pair of inverters and each power supply connection to that latch; and
  at least one 1:2 N demultiplexer formed on the semiconductor substrate, with each 1:2 N demultiplexer having a neural stimulation signal input and an integer number N of addressing inputs, and with the N addressing inputs being connected to the outputs of a set of N of the plurality of latches to receive N bits of the digital addressing signal stored in the set of N latches to program that 1:2 N demultiplexer and thereby connect the neural stimulation signal input to one of 2N outputs for that 1:2 N demultiplexer.

9. The demultiplexer circuit of claim 8 wherein a bi-phasic current signal is provided to the neural stimulation signal input of the at least one 1:2 N demultiplexer, and each output of the at least one 1:2 N demultiplexer is connected to a neural stimulation electrode.

10. The demultiplexer circuit of claim 8 wherein the bridge rectifier comprises a plurality of interconnected complementary metal-oxide semiconductor (CMOS) transistors.

11. The demultiplexer circuit of claim 8 where N is an integer number in the range of 2 to 4.

12. The demultiplexer circuit of claim 8 wherein each latch includes a reverse-biased diode connected between the input of the first pair of inverters and each power supply connection to that latch, and another reverse-biased diode connected between the output of the first pair of inverters and each power supply connection to that latch.

13. The demultiplexer of claim 12 wherein each latch includes a pair of diodes connected in series between the ac-coupled input and the output of the first pair of inverters, with the pair of diodes being connected in a cathode-to-cathode configuration or in an anode-to-anode configuration.

14. The demultiplexer circuit of claim 8 wherein a plurality of electrical vias are formed through the semiconductor substrate, with the electrical vias being connected at one end thereof to the 2N outputs of the at least one 1:2 N demultiplexer, and with an opposite end of each electrical via being electrically connectable to a neural stimulation electrode.

15. The demultiplexer of claim 8 wherein each 1:2 N demultiplexer comprises a plurality of digital logic gates having inputs of the N bits of the digital addressing signal and having outputs which are connected to N transmission gates, with the outputs of the digital logic gates being used to switch one of the N transmission gates to connect the neural stimulation signal input for that 1:2 N demultiplexer to one of the 2N outputs for that 1:2 N demultiplexer.

16. A demultiplexer circuit formed on a semiconductor substrate, comprising:
  a power supply having an energy storage capacitor and a bridge rectifier both formed on the semiconductor substrate, with the power supply receiving an alternating-current (ac) input voltage to generate therefrom all direct-current (dc) electrical power to operate the demultiplexer circuit;
  a plurality of latches formed on the semiconductor substrate, with each latch having an ac-coupled input wherein a digital addressing signal is received one bit at a time, with each bit of the digital addressing signal being stored in that latch and provided to an output thereof until such time as a subsequent bit of the digital addressing signal is received at the ac-coupled input of that latch; and
  at least one 1:2 N demultiplexer formed on the semiconductor substrate, with each 1:2 N demultiplexer having a neural stimulation signal input and an integer number N of addressing inputs, and with the N addressing inputs being connected to the outputs of a set of N of the plurality of latches to receive N bits of the digital addressing signal stored in the set of N latches to program that 1:2 N demultiplexer and thereby connect the neural stimulation signal input to one of 2N outputs for that 1:2 N demultiplexer;
  wherein the semiconductor substrate includes a silicon-on-insulator (SOI) substrate having a monocrystalline silicon base and a monocrystalline silicon layer with an oxide layer being located between the monocrystalline silicon base and the monocrystalline silicon layer.

17. The demultiplexer circuit of claim 16 wherein a bi-phasic current signal is provided to the neural stimulation signal input of the at least one 1:2 N demultiplexer, and each output of the at least one 1:2 N demultiplexer is connected to a neural stimulation electrode.

18. The demultiplexer circuit of claim 16 wherein the bridge rectifier comprises a plurality of interconnected complementary metal-oxide semiconductor (CMOS) transistors.

19. The demultiplexer circuit of claim 16 where N is an integer number in the range of 2 to 4.

20. The demultiplexer circuit of claim 16 wherein a plurality of electrical vias are formed through the semiconductor substrate, with the electrical vias being connected at one end thereof to the 2N outputs of the at least one 1:2 N demultiplexer, and with an opposite end of each electrical via being electrically connectable to a neural stimulation electrode.

21. The demultiplexer circuit of claim 16 wherein each 1:2 N demultiplexer comprises a plurality of digital logic gates having inputs of the N bits of the digital addressing signal and having outputs which are connected to N transmission gates, with the outputs of the digital logic gates being used to switch one of the N transmission gates to connect the neural stimulation signal input for that 1:2 N demultiplexer to one of the 2N outputs for that 1:2 N demultiplexer.

* * * * *